(12) United States Patent
Hegi et al.

(10) Patent No.: US 8,463,400 B2
(45) Date of Patent: Jun. 11, 2013

(54) SYSTEM AND METHOD FOR PROGRAMMING AN IMPLANTABLE SPINAL CORD STIMULATION SYSTEM

(75) Inventors: Peter B. Hegi, Dallas, TX (US); Jonathan Ruais, McKinney, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 157 days.

(21) Appl. No.: 12/789,921

(22) Filed: May 28, 2010

(65) Prior Publication Data

US 2010/0305660 A1 Dec. 2, 2010

Related U.S. Application Data

(60) Provisional application No. 61/182,590, filed on May 29, 2009.

(51) Int. Cl.
*A61N 1/05* (2006.01)

(52) U.S. Cl.
USPC .............................. 607/117; 607/59

(58) Field of Classification Search
USPC .......................... 607/59, 116, 117
See application file for complete search history.

(56) References Cited

U.S. PATENT DOCUMENTS

| | | | |
|---|---|---|---|
| 5,938,690 A * | 8/1999 | Law et al. | 607/46 |
| 6,308,102 B1 | 10/2001 | Sieracki et al. | |
| 7,555,346 B1 | 6/2009 | Woods et al. | |
| 2006/0259079 A1 | 11/2006 | King | |
| 2006/0259099 A1 | 11/2006 | Goetz et al. | |

OTHER PUBLICATIONS

North, et al., "Spinal Cord Stimulation Electrode Design: Prospective, Randomized, Controlled Trial Comparing Percutaneous and Laminectomy Electrodes—Part I: Technical Outcomes," Neurosurgery, Aug. 2002, pp. 381-390, vol. 51, No. 2.
North, et al., "Automated, Patient-Interactive, Spinal Cord Stimulator Adjustment: A Randomized Controlled Trial," Neurosurgery, Mar. 2003, pp. 572-580, vol. 52, No. 3.

* cited by examiner

*Primary Examiner* — Joseph Dietrich

(57) ABSTRACT

In one embodiment, a method for facilitating programming of an implantable pulse generator (IPG) by an external programming device, the method comprises: receiving input from a user by the external programming device to calibrate electrode combinations at a plurality of locations along one or more stimulation leads implanted within the epidural space of a patient; controlling the IPG by the external programmer to apply stimulation to the patient via the electrode combinations; receiving input from a user by the external programming device that indicates values of a respective perception stimulation threshold at each location of the plurality of locations; receiving input from a user by the external programming device that indicates values of a respective bilateral stimulation threshold at each location of the plurality of locations; calculating positions by the external programming device of each of the plurality of locations using the perception stimulation thresholds and the bilateral stimulation thresholds; and displaying calculated positions of the plurality of locations relative to a physiological midline of the patient by the external programming device.

6 Claims, 9 Drawing Sheets

| 1 | 2 | 3 | 4 | 5 | 6 |
|---|---|---|---|---|---|
| PERCEPTION | PERCEPTION | PERCEPTION | PERCEPTION | PERCEPTION | PERCEPTION |
| 2.0 MA | 3.5 MA | 4.0 MA | 4.3 MA | 3.6 MA | 2.5 MA |
| [L][R] | [L][R] | [L][R] | [L][R] | [L][R] | [L][R] |
| BILATERAL | BILATERAL | BILATERAL | BILATERAL | BILATERAL | BILATERAL |
| - MA | 4.2 MA | 4.3 MA | 4.7 MA | 4.2 MA | - MA |
| RATIO | RATIO | RATIO | RATIO | RATIO | RATIO |
| 2 | 1.20 | 1.08 | 1.09 | 1.17 | 2 |
| X-COORDINATE | X-COORDINATE | X-COORDINATE | X-COORDINATE | X-COORDINATE | X-COORDINATE |
| -1 | -0.20 | +0.08 | -0.09 | +0.17 | 1 |

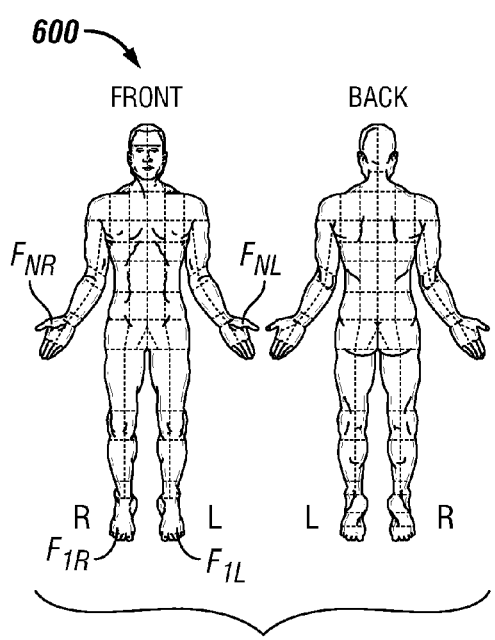
FIG. 6A
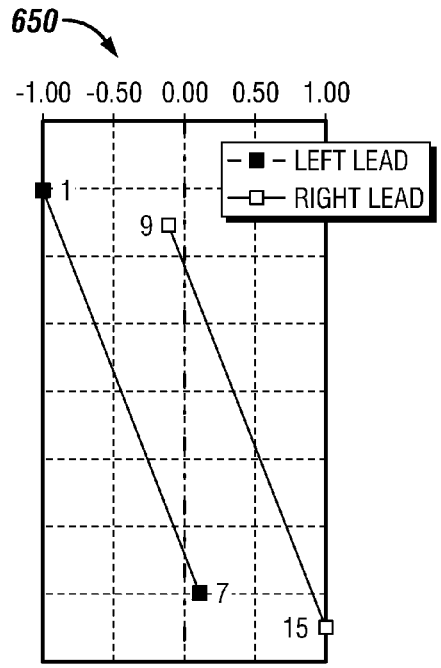
FIG. 6C
625 ↘
| LEFT LEAD OFFSET | 0 |
|---|---|
| RIGHT LEAD OFFSET | -0.5 |
| LEAD | CATHODE # | ELECTRODE POSITION | Y-COORDINATE | LEFT COUNT (L) | RIGHT COUNT (R) | X-COORDINATE |
|---|---|---|---|---|---|---|
| LEFT | 1 | 1 | -1 | 5 | 0 | -1.0 |
| LEFT | 7 | 7 | -7 | 16 | 18 | 0.1 |
| RIGHT | 9 | 1 | -1.5 | 18 | 16 | -0.1 |
| RIGHT | 15 | 7 | -7.5 | 0 | 3 | 1.0 |
FIG. 6B

SYSTEM AND METHOD FOR PROGRAMMING AN IMPLANTABLE SPINAL CORD STIMULATION SYSTEM

CROSS-REFERENCE TO RELATED APPLICATIONS

This application claims the benefit of U.S. Provisional Application No. 61/182,590, filed May 29, 2009, which is incorporated herein by reference.

TECHNICAL FIELD

This application is generally related to programming stimulation parameters of an implantable spinal cord stimulation system.

BACKGROUND

Neurostimulation systems are devices that generate electrical pulses and deliver the pulses to nerve tissue to treat a variety of disorders. Spinal cord stimulation (SCS) is the most common type of neurostimulation. In SCS, electrical pulses are delivered to nerve tissue in the spine typically for the purpose of chronic pain control. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated nerve tissue. Specifically, applying electrical energy to the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

SCS systems generally include a pulse generator and one or more leads. A stimulation lead includes a lead body of insulative material that encloses wire conductors. The distal end of the stimulation lead includes multiple electrodes that are electrically coupled to the wire conductors. The proximal end of the lead body includes multiple terminals, which are also electrically coupled to the wire conductors, that are adapted to receive electrical pulses. The distal end of a respective stimulation lead is implanted within the epidural space to deliver the electrical pulses to the appropriate nerve tissue within the spinal cord that corresponds to the dermatome(s) in which the patient experiences chronic pain. The, stimulation leads are then tunneled to another location within the patient's body to be electrically connected with a pulse generator or, alternatively, to an "extension."

The pulse generator is typically implanted within a subcutaneous pocket created during the implantation procedure. In SCS, the subcutaneous pocket is typically disposed in a lower back region, although subclavicular implantations and lower abdominal implantations are commonly employed for other types of neuromodulation therapies.

The pulse generator is typically implemented using a metallic housing that encloses circuitry for generating the electrical pulses, control circuitry, communication circuitry, a rechargeable battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on a stimulation lead.

SUMMARY

In one embodiment, a method for facilitating programming of an implantable pulse generator (IPG) by an external programming device, the method comprises: receiving input from a user by the external programming device to calibrate electrode combinations at a plurality of locations along one or more stimulation leads implanted within the epidural space of a patient; controlling the IPG by the external programmer to apply stimulation to the patient via the electrode combinations; receiving input from a user by the external programming device that indicates values of a respective perception stimulation threshold at each location of the plurality of locations; receiving input from a user by the external programming device that indicates values of a respective bilateral stimulation threshold at each location of the plurality of locations; calculating positions by the external programming device of each of the plurality of locations using the perception stimulation thresholds and the bilateral stimulation thresholds; and displaying calculated positions of the plurality of locations relative to a physiological midline of the patient by the external programming device.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

BRIEF DESCRIPTION OF THE DRAWINGS

FIG. 6A depicts a "stim man" representation for use in a user interface according to one representative embodiments.

FIG. 6B depicts table that includes data calculated according to one representative embodiment and FIG. 6C depicts a plot of electrode positions according to data shown in FIG. 6B according to one representative embodiment.

DETAILED DESCRIPTION

Figure 1:
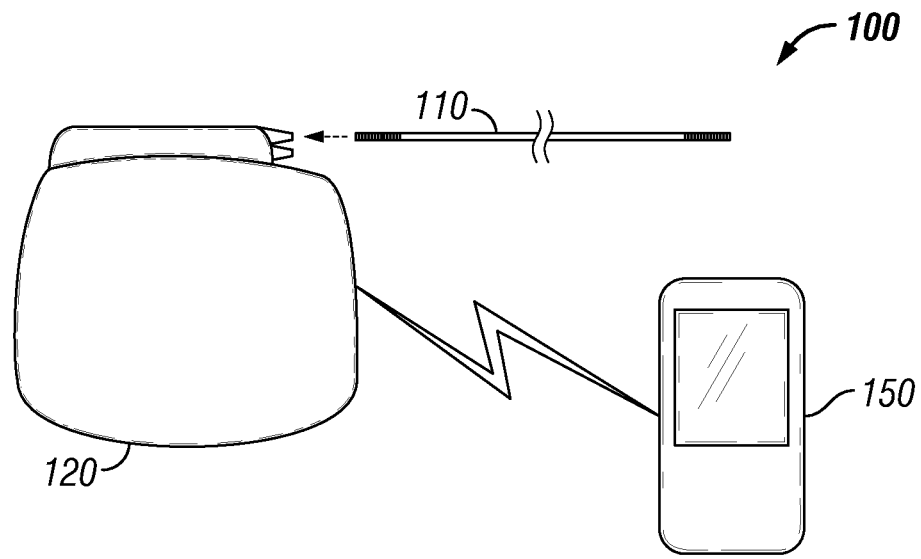
FIG. 1 depicts a spinal cord stimulation system according to one representative embodiment.

FIG. 1 depicts stimulation system 100 for spinal cord stimulation according to one embodiment. Stimulation system 100 includes pulse generator 120. Examples of commercially available pulse generators are the EON® and EON® MINI pulse generators available from St. Jude Medical Neuromodulation Division. Pulse generator 120 is typically implemented using a metallic housing that encloses circuitry for generating electrical pulses for application to neural tissue of the patient. Control circuitry, communication circuitry, and a rechargeable battery (not shown) are also typically included within pulse generator 120. Pulse generator 120 is usually implanted within a subcutaneous pocket created under the skin by a physician.

Pulse generator 120 is adapted to accept one or more stimulation leads. As shown in FIG. 1, percutaneous lead 110 is electrically coupled to the circuitry within pulse generator 120 by inserting the proximal end of lead 110 into the header of pulse generator 120. Percutaneous lead 110 comprises a plurality of "terminals" and a plurality of "electrodes." The terminals are adapted to connect to electrical connectors within the header of pulse generator 120 or within a connector portion of an "extension" lead as is known in the art. The electrodes are adapted to be placed in contact with tissue of the body for application of electrical pulses. Although a percutaneous leads is shown in FIG. 1, paddle-style leads having any suitable number of columns and rows of electrodes may be also be employed according to some embodiments. For example, a PENTA™ paddle lead, available from St. Jude Medical Neuromodulation Division (Plano, Tex.) may be employed where a display of the five columns of electrodes of the lead are displayed along with a representation of the physiological midline relative to the electrodes according to any of the methodologies discussed herein.

External controller 150 is used to control the operations of pulse generator 120. External controller 150 preferably comprises a microprocessor, microcontroller, digital signal processor, or other processor (not shown) for controlling the operations of external controller 150. Further, software code (not shown) is stored in memory of external controller 150 to control the operations of the external controller 150. External controller 150 conducts wireless communications with pulse generator 120 to transmit operational parameters to pulse generator 150. The operational parameters may define or select pulse amplitudes, pulse widths, pulse frequencies, stim set data, multi-stim set programs, and/or the like. External controller 150 provides one or more graphical user interfaces to facilitate the control of pulse generator 120. User interfaces according to some embodiments will be discussed in greater detail below.

Figure 2A:
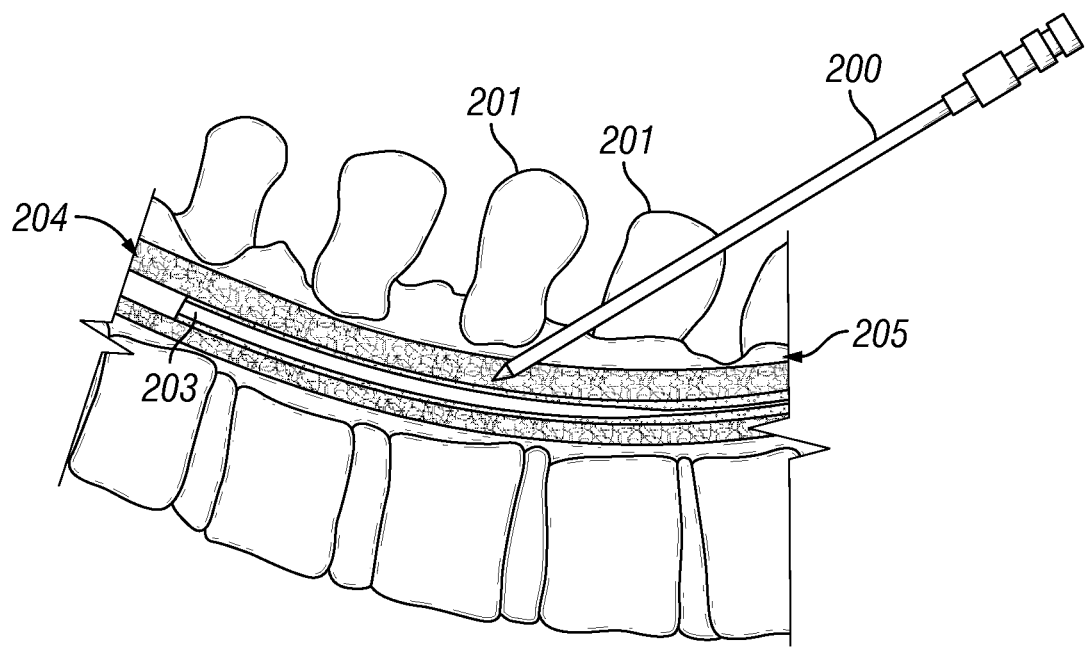
FIGS. 2A and 2B depict implantation of a stimulation lead into the epidural space of the patient.
Figure 2B:
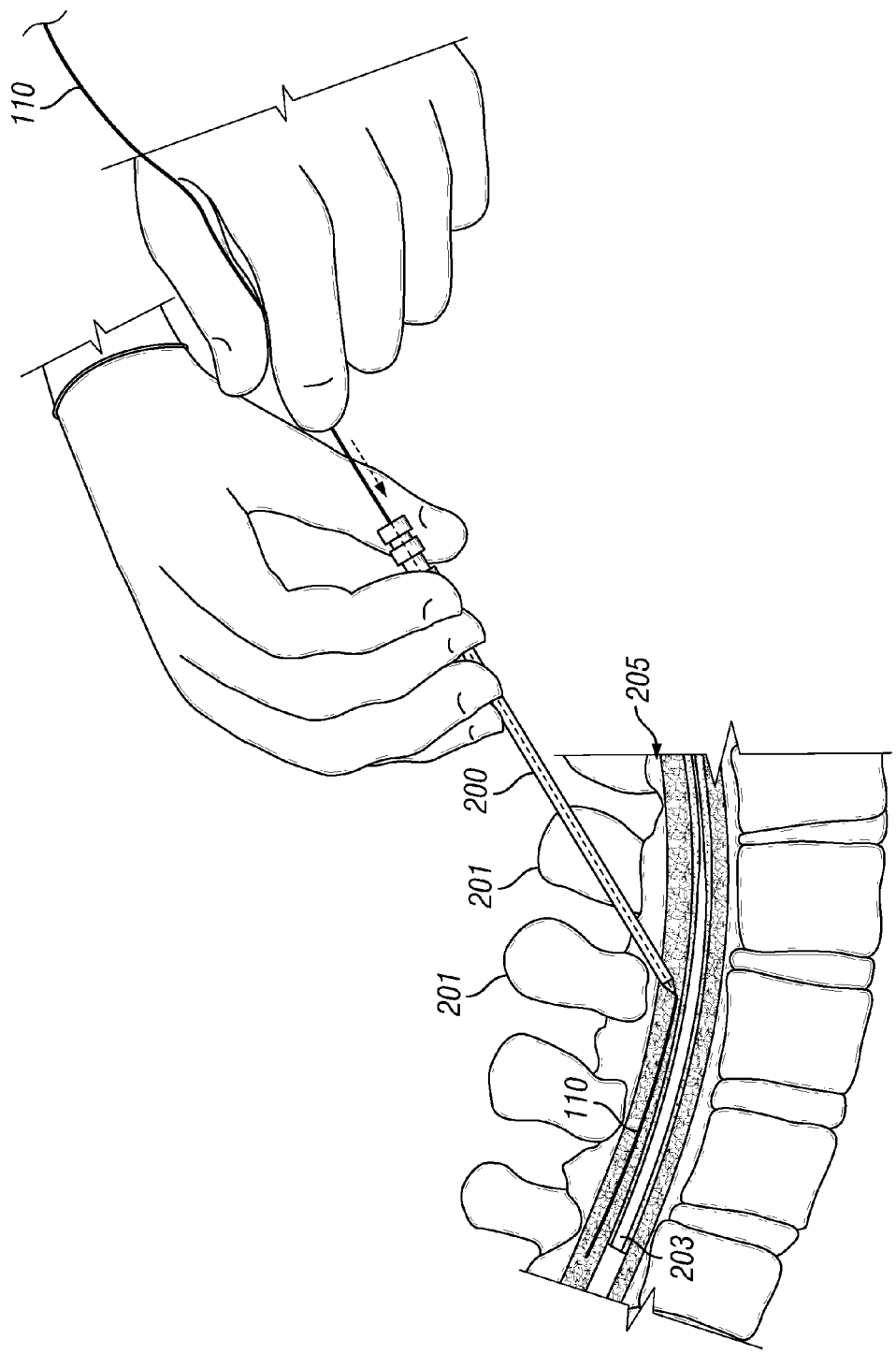

FIGS. 2A and 2B depict implantation of percutaneous lead 110 into the epidural space of a patient. During an implantation procedure, a physician typically initially inserts hollow needle 200 (with an internal stylet to prevent tissue coring) into the epidural space 204. Specifically, the physician selects a vertebral level that corresponds to the area of the patient's body afflicted by chronic pain. For example, vertebral levels L1 and L2 are commonly selected for chronic pain in both the lower back and lower extremities. Needle 200 is advanced using a paramedian approach, beginning laterally relative to spinal processes 201 and caudal to the desired implant site. Needle 200 is directed at an angle of entry less than forty-five degrees from the plane defined by the epidural space 204 to subsequently ease the advancement of lead 110 into the epidural space 204. The needle 200 is advanced by the physician until the needle 200 penetrates through the ligamentum flavum 205. Entry of the needle 200 into the epidural space 204 can be verified using standard methods such as the "loss of resistance" technique.

The stylet is then removed from the needle 200 and the percutaneous lead 110 is threaded through the hollow interior of the needle 200 into the epidural space 204 as shown in FIG. 2B. The physician typically positions the percutaneous lead 110 2 mm-3 mm right or left of midline of spinal cord 203 such that the lead 110 is positioned on the same side of the body as the patient's pain. If the percutaneous lead 110 is positioned too far laterally relative to spinal cord 203, the patient may experience painful sensations due to stimulation of nerve roots. Also, if pain is experienced on both sides of the patient's body, the physician may implant two percutaneous leads 110 with one lead 110 on each respective side of midline of the spinal cord 203.

After implantation of leads 110, a clinician typically programs pulse generator 120 to apply stimulation pulses to the patient in order to optimize the patient's response to the stimulation therapy. In general, the clinician moves stimulation up and down (cephalo-caudal movement) and varies stimulation intensity (e.g., pulse amplitude) in order to obtain paresthesia over an area that most closely matches the painful area of the patient's body, provides adequate pain-relief, and avoids painful stimulation (e.g., stimulation of nerve roots).

In many cases, the programming process is like programming a black box. That is, programming parameters are changed and patient feedback is obtained. The process is repeated until an acceptable set of therapy parameters are obtained. Experienced clinicians can augment a strictly trial and error approach with several techniques. For example, experienced clinicians use the anatomical spinal midline as a proxy for the physiological midline and modify stimulation parameters relative to the midline. However, this technique is imperfect, because the physiological midline varies from the anatomical midline in approximately 40% of patients. Also, stimulation leads are not necessarily oriented parallel to the midline upon implantation. Due to such limitations, movement of stimulation cephalo-caudally (by selectively activating electrodes of one or more stimulation leads 110) does not always elicit a comparable cephalo-caudal movement in paresthesia in a patient.

Representative embodiments implement controller 150 to provide one or more user interfaces that display the orientation of one or more leads relative to the physiological midline to assist a clinician in selecting stimulation parameters for pulse generator 120. Controller 150 further implements an automated stimulation test sequence for acquiring data to permit the orientation of the lead(s) relative to midline to be determined. By providing such information pertaining to lead orientation to a clinician, the clinician is more readily able to correlate changes in electrode activation during stimulation to changes in paresthesia experienced by the patient. Thereby, a clinician may arrive at an effective stimulation therapy in a more efficient manner.

Figure 3:
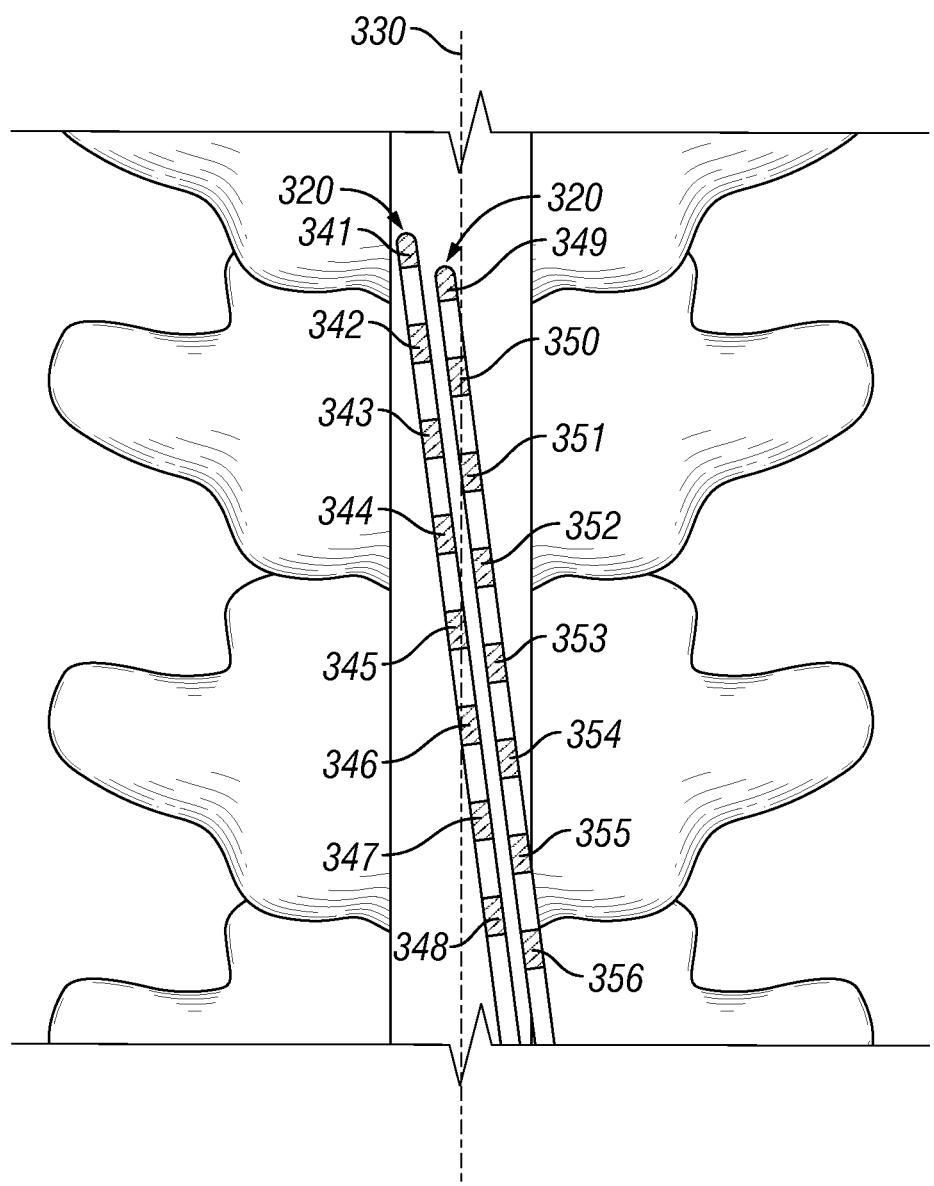
FIG. 3 depicts stimulation leads implanted within the epidural space relative to the physiological midline.
Figure 4A:
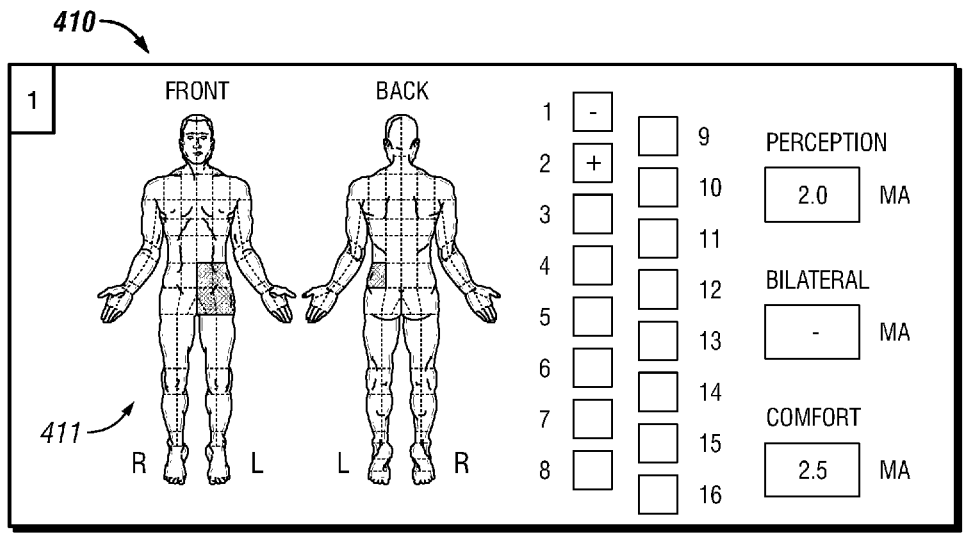
FIGS. 4A-4F depict respective user interface screens of a programming device according to one representative embodiment.
Figure 4B:
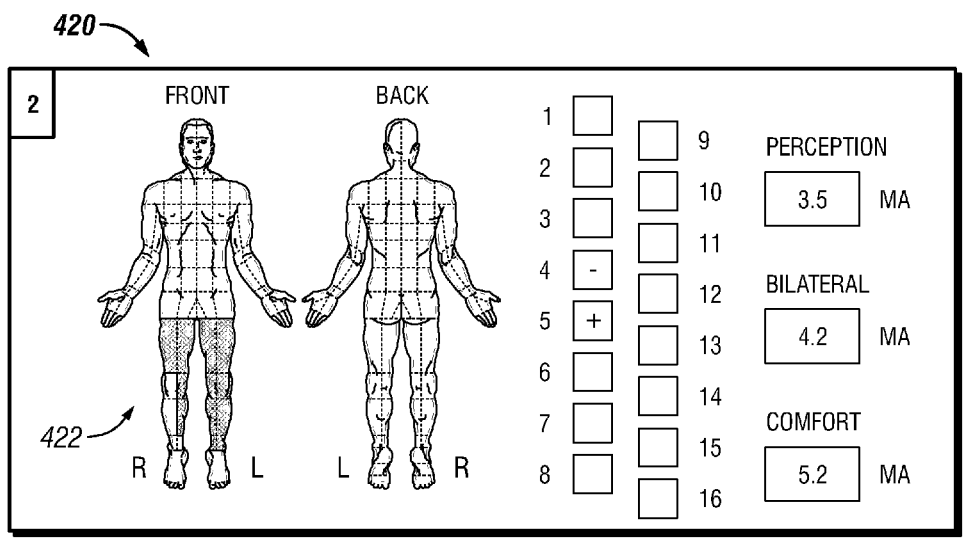
Figure 4C:
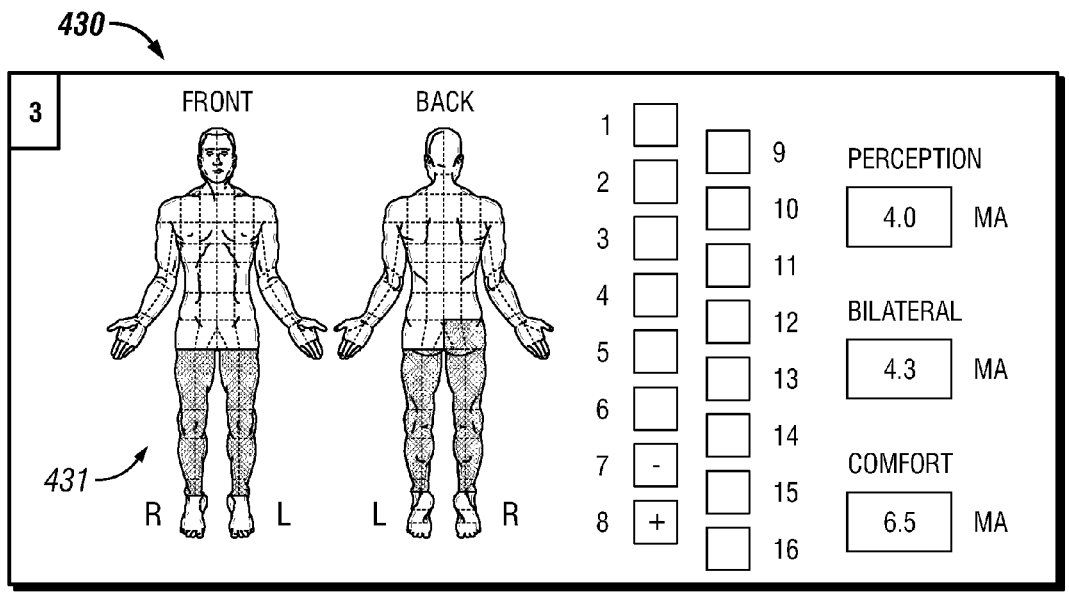
Figure 4D:
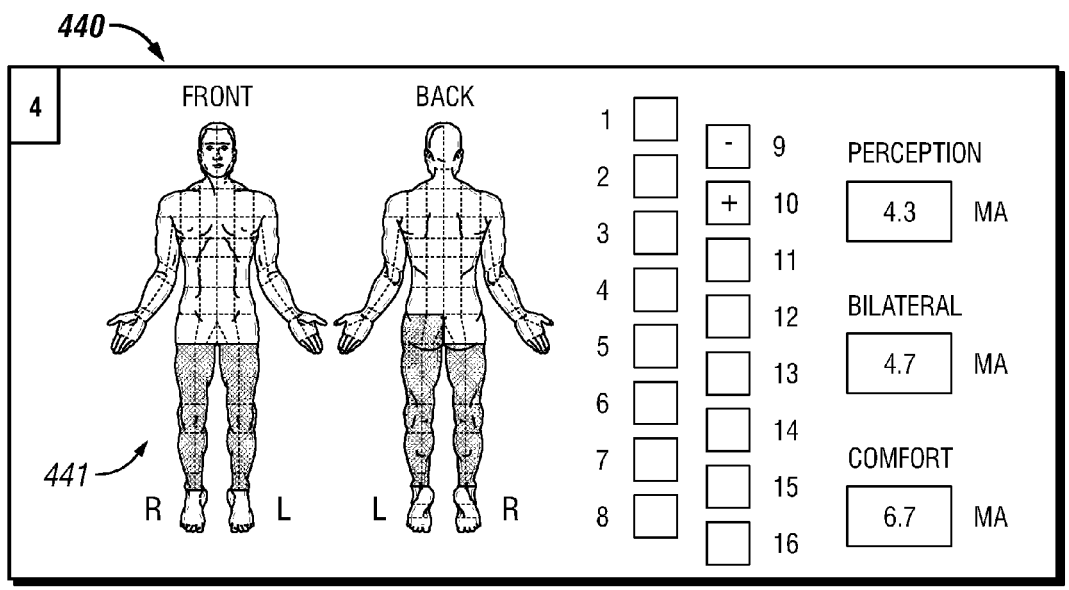
Figure 4E:
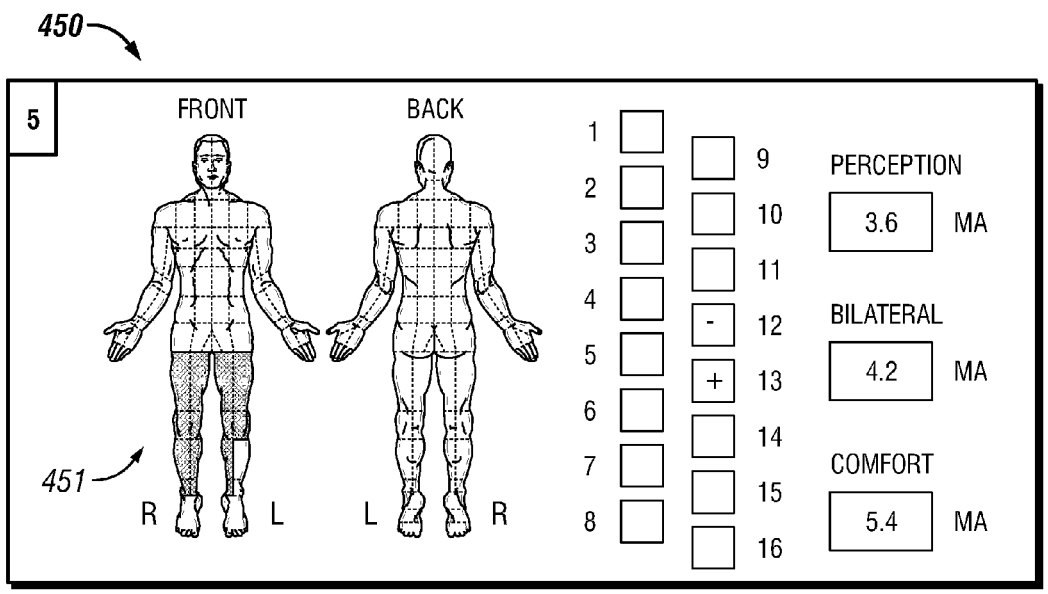
Figure 4F:
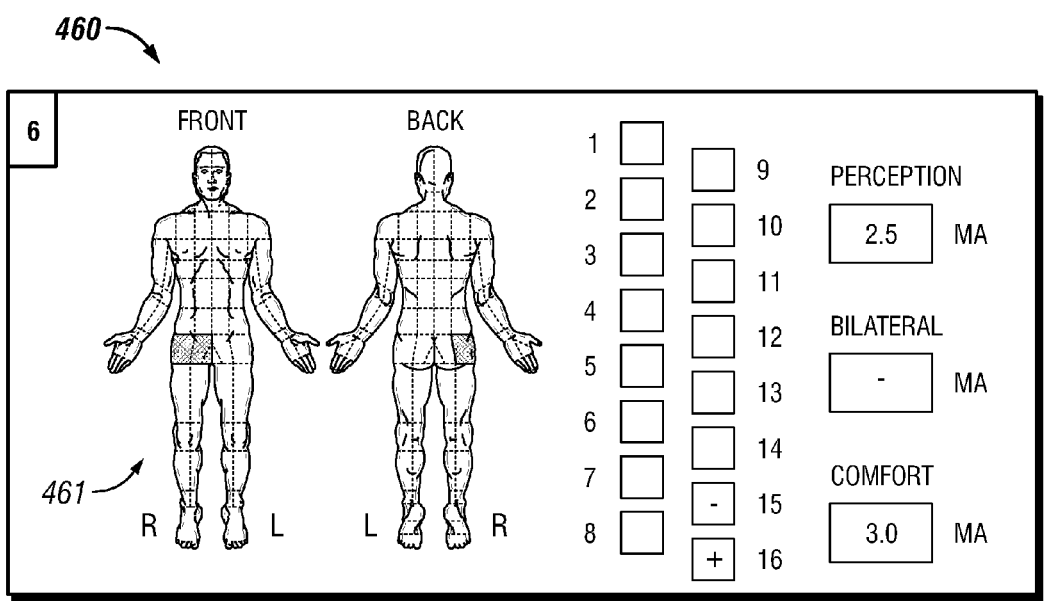

To illustrate concepts according to some embodiments, FIG. 3 depicts stimulation leads 310 and 320 positioned relative to physiological midline 330. Electrodes 341-348 are disposed along the length of lead 310. Electrodes 349-356 are disposed along the length of lead 320. As shown in FIG. 3, leads 310 and 320 are not oriented in a parallel arrangement with midline 330. Instead, at the T-10 level, electrode 348 of lead 310 and electrode 356 of lead 320 are positioned right of midline 330. Slightly above the T-9 level, electrode 341 of lead 310 and electrode 349 are disposed to the left of midline 330. The arrangement of stimulation leads 310 and 320 as shown in FIG. 3 will cause a patient to experience bilateral stimulation thresholds at different amplitudes for different electrode combinations along the length of the leads.

Some representative embodiments measure perception amplitude values and bilateral amplitude values and calculate the ratio of these values in determining the relative orientation of one or more leads relative to the physiological midline of a patient (such as the arrangement of leads 310 and 320 relative to midline 330 as shown in FIG. 3). In one embodiment, these values are determined during a calibration procedure (conventional calibration procedures determine perception thresholds amplitude, comfortable amplitude values, maximum tolerable amplitude values, and possibly other values as is well known in the art). Various ones of these values may also be used to balance or normalize stimulation applied to the patient as is well known in the art. For example, perception amplitude and other values may be used to define a permissible stimulation range and stimulation increment for stimulation applied by the respective electrode combination. These values may alternatively be determined using any suitable programming process or protocol.

During a programming procedure, for each selected electrode combination, the amplitude is controllably increased or ramped until the patient first perceives paresthesia in response to stimulation applied via the respective electrode combination. This amplitude defines the perception amplitude value for the respective electrode combination. Also, the side (left, right, or even both sides, if applicable) of the body on which paresthesia is first experienced for the electrode combination is recorded. That is, the patient may first experience paresthesia during amplitude ramping on the left side, on the right side, or on both sides simultaneously.

The amplitude is further increased or ramped until the patient experiences paresthesia on both sides of the patient's body (assuming that the initial perception was not experienced bilaterally). This amplitude defines the bilateral amplitude value for the respective electrode combination. The bilateral amplitude need not be determined for all electrode combinations. For example, if during the programming procedure, a comfort amplitude value determined for a selected electrode combination is reached before the bilateral paresthesia is experienced, the actual bilateral amplitude value need not be found for some embodiments.

FIGS. 4A-4F respectively depict programmer interface screens 410-460 provided by controller 150 according to one representative embodiment. Each screen of screens 410-460 depicts various stimulation amplitude values corresponding to a respective electrode combination. The "+" symbol refers to an anode location along the lead(s) and the "−" symbol refers to a cathode location. As respectively shown in FIGS. 4A-4C, selected electrode combinations are disposed at the ends of the left stimulation lead and at the middle of the left stimulation lead. As respectively shown in FIGS. 4D-4F, corresponding electrode combinations are disposed at the ends of the right stimulation lead and at the middle of the right stimulation lead.

Each screen depicts a respective "stim map" (shown as maps 411, 421, 431, 441, 451, and 461) which shows various bodily regions corresponding to paresthesia experienced by the patient. Also, each screen includes graphical controls that display respective programming parameters (perception and comfort amplitude values) and the bilateral amplitude value.

According to one embodiment, the various programming parameters are utilized to provide a plot of the electrodes relative to physiological midline of a patient. In one preferred embodiment, the following logic and formulas are employed to depict a position of a respective electrode:

---

Ratio:
    IF (Bilateral==UNDEFINED) {Ratio = 2;}
    ELSE {Ratio = min(2, Bilateral/Perception);}
Y coordinate of the electrode:
    Y = − (locus of stimulation) + Lead Offset;
X coordinate:
    IF (Perception Location == Left_and_Right) {X = 0;}
    ELSE {
        IF (Perception Location == Left) {X = 1 − Ratio;}
        ELSE {X = Ratio−1;}
    }

--- where X=0.0 is defined as the spinal cord physiological midline and Y refers to the approximate center longitudinal position as located relative to the cathode and anode(s) (if any). The locus of stimulation may also be varied depending upon the applied active electrode combination. For example, more complicated anode/cathode patterns may produce an electrical field with a locus of stimulation that is offset relative to the center position between the anode(s) and cathode(s). The discussed calculations may include a sub-calculation or look-up operation to accommodate to such positions of the applied electrical field.

Figures 5A, 5B:
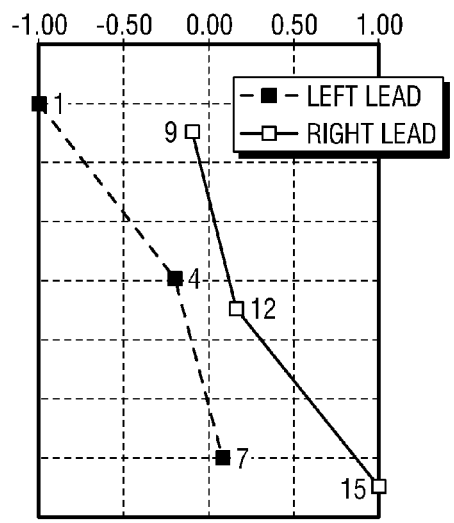
FIG. 5A depicts a table that includes data calculated according to one representative embodiment.
FIG. 5B depicts a plot of electrode positions relative to the physiological midline of a patient according to the data shown in FIG. 5A.

FIG. 5A depicts table 500 that comprises calculated values for the electrodes and programming values previously shown in FIGS. 4A-4F. FIG. 5B depicts chart 510 corresponding to the calculated X and Y coordinates for the various electrodes according to the values in table 500 of FIG. 5A. As shown in FIG. 5B, the connections between the various electrode points roughly corresponds to the alignment of the stimulation leads relative to each other. Also, the relative distance to the physiological midline is shown. Accordingly, a clinician may more readily appreciate the relationship between a given electrode combination and the paresthesia that the patient would experience from stimulation at the electrode combination.

In other embodiments, the relative size of areas on the left and right side of the patient in which the patient experiences paresthesia are utilized to estimate the position of an electrode combination relative to the physiological midline. In some embodiments, one or more user interfaces are presented by external controller 150 that permit a patient or clinician to indicate locations on the patient's body where paresthesia is experienced in response to stimulation. Referring to FIG. 6A, "stim man" representation 600 presents a view of the human body divided into various sub-regions on the front, back, left, and right sides of the patient.

In operation, stimulation is provided to the patient via a respective electrode combination along one of the stimulation leads. The patient indicates (e.g., via input with a stylus) which bodily regions are affected by the stimulation. In one embodiment, the ratio of the number of affected sub-regions on the left side of the patient to the number of affected sub-regions on the right side of the patient is employed to estimate the position of the respective electrode combination relative to the physiological midline. As shown in FIG. 6A, a variable is preferably defined for each individual sub-region. $F_{nL}$ represents the effect of stimulation in location "n" on the left side of the patient. $F_{nR}$ represents the effect of stimulation in location "n" on the right side of the patient. In one embodiment, each variable is set to equal "1" if paresthesia is experienced by the patient in the respective sub-region and is set equal to "0" if the paresthesia is not experienced.

In one embodiment, the following summations are defined:
Left Factor (L)=$\Sigma_{n=1}^{N} F_{nL}$;
Right Factor (R)=$\Sigma_{n=1}^{N} F_{nR}$ In this embodiment, the respective electrode position is then determined as follows (where X=0.0 is defined as the physiological midline):
Y coordinate: Y=−(locus of stimulation)+Lead Offset;
X coordinate: IF (L>R) {X=R/L−1;} ELSE {X=1−L/R;}

Following this methodology, FIG. 6B depicts table 625 that includes electrode positions, Y-coordinates, L count values, R count values, and X coordinates according to one embodiment. FIG. 6C depicts a corresponding plot 650 of electrodes of stimulation leads relative to the physiological midline according to the data shown in FIG. 6B. Although in one embodiment, the physiological midline is shown to be oriented straight "up and down" in the display and the electrodes are shown in a sloped orientation, other variations may be employed. For example, the electrodes may be displayed in a straight "up and down" configuration and the physiological midline may be oriented using a sloped, slightly curved, or other suitable representation according to the calculated data. It shall be appreciated that any suitable number of data points may be employed to plot the position of electrodes on leads according to this methodology. It shall be further appreciated that the calculation may employ bodily sub-regions on the front, back, or both front and back of the patient.

Figure 7:
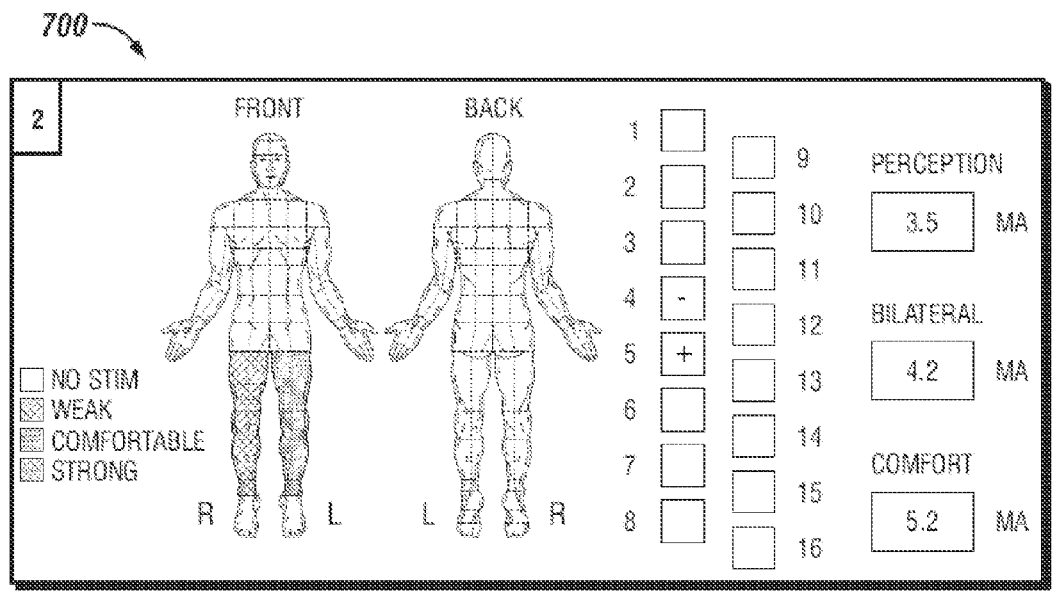
FIG. 7 depicts a screen for presentation by an external controller according to one representative embodiment.

In another embodiment, weighting factors could be employed for the left factor "L" and the right factor "R" according to the strength of the paresthesia experienced by the patient in the respective bodily sub-region. FIG. 7 depicts screen 700 for presentation by external controller 150. Screen 700 permits a patient or clinician to enter or otherwise define the relative strength of stimulation in the various bodily sub-regions. In the embodiment shown in FIG. 7, screen 700 permits a patient to indicate whether the patient experiences no stimulation, weak stimulation, comfortable stimulation, or strong stimulation in each of the defined bodily sub-regions.

For the purpose of calculating electrode position relative to the physiological midline, the variables $F_{nL}$ and $F_{nR}$ are given the values 0 for no stimulation, 0.5 for weak stimulation, 1.0 for comfortable stimulation, and 1.5 for strong stimulation as examples. The X and Y coordinates are then calculated in the same manner as discussed above in regard to the two-state stimulation embodiment.

Figure 8:
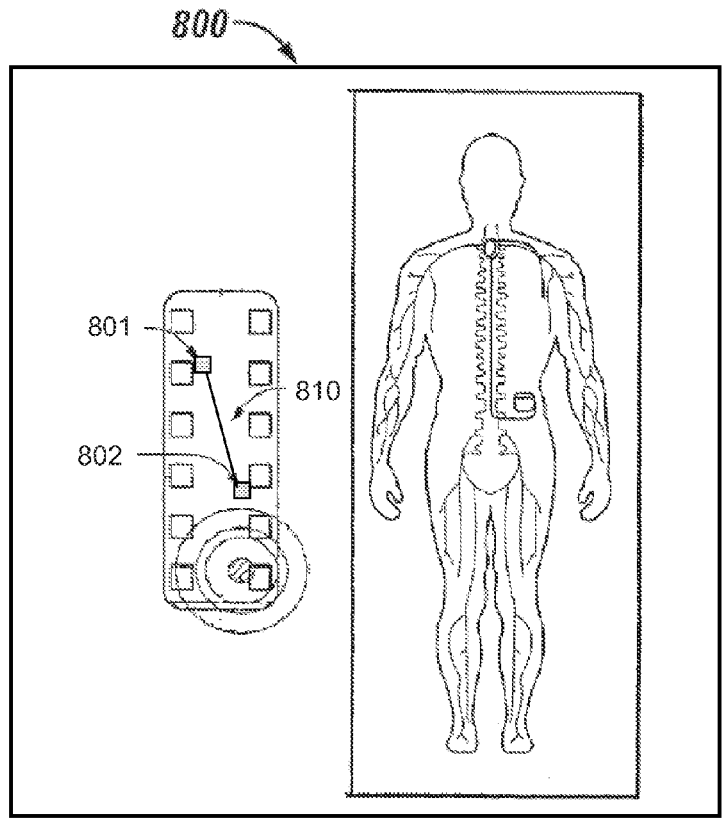
FIG. 8 depicts another screen for presentation to a user according to another representative embodiment.

FIG. 8 depicts screen 800 for presentation by external controller 150. In one embodiment, the clinician or other user is able to use an input device (e.g., touchscreen, stylus, mouse, joystick, etc.) to move a focus of stimulation relative to the various electrodes via screen 800. Also, fractionalization or other suitable current steering techniques (which are known in the art) may be employed to move the focus of stimulation to locations laterally and longitudinally between individual active electrode combinations. In this embodiment, the clinician may enter data points (e.g., data points 801 and 802) which correspond to bilateral locations as determined by suitable calculations and/or by patient feedback. In response thereto, external controller 150 preferably includes representation 810 of the physiological midline as predicted by the various data points.

In another embodiment, electromyogram (EMG) data is used to estimate the relative position of one or more electrodes relative to the physiological midline of a patient. Surface or needle EMG techniques may be employed to obtain the data. Specifically, a plurality of suitable electrodes or needles are preferably placed on the right and left sides of a patient which are, in turn, coupled to suitable EMG circuitry to generate the EMG data. The electrodes or needles are preferably arranged in an approximately symmetrical or otherwise corresponding manner about the patient's left and right sides. Spinal cord stimulation is applied to the patient at a relatively high level such that motor recruitment is obtained (while the patient is provided with suitable anesthesia). When motor recruitment occurs, the patient will experience muscle contractions. The strength of the motor response on the left and right sides of the patient may be compared to each other to estimate at particular electrode combination's position relative to the physiological midline. For example, the ratio between the sum of the energy in the EMG data from the left side of the patient and the sum of the energy in the EMG data from the right side of the patient can be calculated to determine the estimated location. The sum of the energy can be determined using conventional digital signal processing techniques. In other embodiments, other digital signal processing metrics may be calculated using the EMG data; such as root-mean-square (RMS) calculations, for the purpose of comparing the effect of stimulation on the left and right sides of the patient.

When implemented in software on the external controller 150, the various elements or components of representative embodiments are the code or software segments adapted to perform the respective tasks. For each of the tasks discussed above in regard to user interfaces, calculations related to electrode positions, and display of electrode positions relative to the midline, segments of software code are preferably provided in memory of external controller 150 to perform the various tasks. Software code segments stored in external controller 150 are also provided to perform conventional tasks such as communicating control parameters to IPG 120, receiving user input (e.g., designating sub-regions of paresthesia), setting programming parameters, etc. Although the code is preferably provided in a single device, code to perform these tasks could alternatively be executed one multiple platforms (collectively functioning as "an external programming device") including a laptop or handheld computer belonging to the patient and/or clinician. The segments of software code can be implemented in any suitable programming language ranging from low level machine instructions to higher level programming scripts executed by a suitable interpreter as examples. The program(s) and/or code segments can be stored in any suitable type of memory. Also, the program(s) and/or code segments can be received or downloaded from or through any suitable medium/media or network(s).

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

The invention claimed is:

1. A method for facilitating programming of an implantable pulse generator (IPG) by an external programming device, the method comprising:

receiving input from a user by the external programming device to program electrode combinations at a plurality of locations along one or more stimulation leads implanted within the epidural space of a patient;

controlling the IPG by the external programmer to apply stimulation to the patient via the electrode combinations;

receiving input from a user by the external programming device that indicates values of a respective perception stimulation threshold at each location of the plurality of locations, wherein the perception stimulation threshold represents a minimal stimulation level that causes perception of stimulation in the patient on either side of the body of the patient;

receiving input from a user by the external programming device that indicates values of a respective bilateral stimulation threshold at each location of the plurality of locations, wherein the bilateral stimulation threshold represents a minimal stimulation level that causes the perception of stimulation on both sides of the body of the patient;

calculating positions by the external programming device of each of the plurality of locations using the perception stimulation thresholds and the bilateral stimulation thresholds; and displaying calculated positions of the plurality of locations relative to a physiological midline of the patient's spinal cord by the external programming device.

2. The method of claim 1 wherein the one or more stimulation leads comprises two percutaneous stimulation leads implanted bilaterally in the epidural space of the patent.

3. The method of claim 2 wherein the plurality of locations comprises a distal electrode location and a proximal electrode location on each of the two percutaneous stimulation leads.

4. The method of claim 1 wherein the one or more leads comprises a paddle-style stimulation lead.

5. The method of claim 1 wherein the calculating comprises calculating a ratio between a respective bilateral stimulation threshold and a corresponding perception stimulation threshold.

6. The method of claim 1 wherein the external programming device provides one or more graphical user interface screens for entry of data to define the respective perception and bilateral threshold values.

* * * * *